US008208701B2

(12) United States Patent
Lendl

(10) Patent No.: US 8,208,701 B2
(45) Date of Patent: Jun. 26, 2012

(54) METHOD FOR HIGH-RESOLUTION PRESENTATION OF FILIGREE VESSEL IMPLANTS IN ANGIOGRAPHIC IMAGES

(75) Inventor: Markus Lendl, Ottensoos (DE)

(73) Assignee: Siemens Aktiengesellschaft, München (DE)

( * ) Notice: Subject to any disclaimer, the term of this patent is extended or adjusted under 35 U.S.C. 154(b) by 772 days.

(21) Appl. No.: 12/150,216

(22) Filed: Apr. 24, 2008

(65) Prior Publication Data
US 2008/0267475 A1 Oct. 30, 2008

(30) Foreign Application Priority Data

Apr. 24, 2007 (DE) .................... 10 2007 019 328

(51) Int. Cl.
G06K 9/00 (2006.01)
(52) U.S. Cl. ........ 382/128; 382/130; 382/254; 382/284; 382/294
(58) Field of Classification Search .................. 382/128, 382/130, 294, 254, 284
See application file for complete search history.

(56) References Cited

U.S. PATENT DOCUMENTS

| 5,970,119 | A * | 10/1999 | Hofmann | 378/163 |
| 7,844,126 | B2 * | 11/2010 | Mory et al. | 382/254 |
| 2003/0181809 | A1 | 9/2003 | Hall et al. | |
| 2006/0229594 | A1 * | 10/2006 | Francischelli et al. | 606/27 |
| 2008/0045827 | A1 * | 2/2008 | Rongen et al. | 600/407 |
| 2008/0170765 | A1 * | 7/2008 | D'sa et al. | 382/128 |
| 2011/0019892 | A1 * | 1/2011 | Rahn et al. | 382/131 |

FOREIGN PATENT DOCUMENTS

| DE | 10210646 A1 | 10/2003 |
| WO | WO 03043516 A2 | 5/2003 |
| WO | WO 2004051572 A2 | 6/2004 |
| WO | WO 2005104951 A1 | 11/2005 |

OTHER PUBLICATIONS

Hill et al. "Medical image registration," Institute of Physical Publishing, Jun. 12, 2000, pp. 1-45.*
Chiang et al. "Coincident Bit Counting—A New Criterion for Image Registration," IEEE Transactions on Medical Imaging, vol. 12, No. 1, Mar. 1993, pp. 30-38.*
Erik H. W. Meijering, Wiro J. Niessen, Max A. Viergever, "Retrospective Motion Correction in Digital Subtraction Angiography: A Review", IEEE Transactions on Medical Imaging, vol. 18, No. 1, Jan. 1999, pp. 2-21; Magazine; 1999.

* cited by examiner

Primary Examiner — Andrew W Johns
Assistant Examiner — Shefali Goradia

(57) ABSTRACT

The invention relates to a method for high-resolution display of vessel implants in angiographic images, featuring the steps: recording at least two images of an object-catheter combination including catheter markers with a medical imaging method; detection of a region of interest created in the form of an area between the balloon markers which completely contains the object to be registered for each recorded image; coarse registration of the region of interest images by registration of the respective pairs of balloon markers of all recorded images; fine registration of the region of interest image content/of the region of interest image by registration of the region of interest content; and arithmetic averaging across the fine-registered images.

9 Claims, 3 Drawing Sheets

METHOD FOR HIGH-RESOLUTION PRESENTATION OF FILIGREE VESSEL IMPLANTS IN ANGIOGRAPHIC IMAGES

CROSS REFERENCE TO RELATED APPLICATIONS

This application claims priority of German application No. 10 2007 019 328.0 filed Apr. 24, 2007, which is incorporated by reference herein in its entirety.

FIELD OF THE INVENTION

The present invention relates in general to an angiographic imaging method such as is used in medicine in the area of vascular surgery for example, more precisely in diagnostic and interventional cardiology. In such cases the present invention relates especially to a method which allows evaluation of the status during or after the placement of filigree vessel implants (such as stents for example) under the influence of different body movements.

BACKGROUND OF THE INVENTION

In modern (heart) vessel surgery (Percutaneous Transluminal (Coronary) Angioplasty PT(C)A expanding plastics—so-called stents—are inserted) to an increasing extent intravascularly into stenotized vessel sections. This involves implants usually in the form of thin wire meshes (wire diameter only a few hundredths of a millimeter) in rare cases also in the form of small metal or plastic tubes, which prevent a renewed narrowing of the vessel or even worse a closing-off of the vessel at the relevant point by supporting the vessel wall to hold it open.

A stent is introduced either after or during an artificial expansion process e.g. by means of an ablation laser, thrombectomy catheter, etc. mostly however with a balloon catheter. The balloon catheter is introduced via a guidance wire and pumped up with water mixed with contrast media or just with air in order to expand the point in the vessel concerned so that the stent can be introduced subsequent to the removal of the balloon catheter. However if the vessel is already too weak for this, a (new) balloon catheter is introduced which functions in its slightly inflated state as a stent support, in that the stent is pushed over outer membrane of the balloon and is inserted held by the balloon into the narrowed area of the vessel, i.e. implanted. The balloon is deflated and withdrawn. Compared to a surgically much more complicated bypass operation, a catheter-based stent implant represents a quicker, more efficient and also less hazardous implantation method.

An absolute requirement in such cases however is a precise and very good visualization of the stent in the surrounding tissue during and after the implantation, in order to enable both the position and also the instantaneous state (e.g. the degree of unfolding) to be assessed.

The visualizing can be undertaken with a wide diversity of imaging modalities such as computer tomography, fluoroscopy, sonography or magnetic resonance tomography for example, on which however high demands are imposed and which at the current time have still not been satisfactorily resolved.

There are various reasons for the high demands imposed on the angiographic imaging technologies, for example because—as already mentioned—a stent typically consists of a very thin wire mesh (stent mesh diameter in the region of a few hundredths of a millimeter) and a movement within the framework of the wire diameter (during the acquisition of a snapshot) is sufficient to make an image of the stent unusable.

It is also problematic if the thickness of the body tissue to be imaged by x-rays for example is comparatively large and if highly absorbent structures cast shadows over the stent.

Also necessary for good visibility is a sufficient resolution of the object with a sufficiently large quantum flow density where x-ray radiation is used as the imaging technique. As a rule the number of verifiable quantas per detector surface from the x-ray source and the image acquired is not sufficient, since the time $\Delta t$ of a recording process (shot time) must be kept short because of the imprecisions of movement as the time t increases and in addition the power of the x-ray tube is limited. In addition the distance between patient and x-ray detector must be minimized because of the increasingly imprecise movements which in its turn leads to the object of interest (the filigree vessel implant) appearing as an image on a comparatively small area of the detector surface. If a Flat-Panel Detector (FPD) is additionally used as an x-ray detector, converting the x-rays which have penetrated the body directly into an electrical signal (direct converter) under some circumstances its restricted local resolution also comes into play.

All these factors show that an artifact-free visualization, localization, identification and status evaluation of filigree vessel implants still poses a problem, at least with angiographic fluoroscopy.

The current practice is thus either to be satisfied with the result of a standard angiographic examination (as a rule these are 2D projection images, coronal, sagittal or axial 2D-sectional images in the x-ray CT imaging or 3D-representations of the segmented vessel segments incl. embedded vessel implants in the magnetic resonance tomographic imaging) or an attempt is made to make the stent visible through "inter-image postprocessing".

This method represents an arithmetical averaging (over time) of the image data of a number of consecutive similar images (e.g. angiocardiograms of one and the same section of an image). Since objects specifically visualized in PTCA by means of CT or MR angiographic imaging (e.g. balloon catheters and vessel implants with guide wire, guide tube etc.) move very fast because of the movement of the heart, a movement detection is indispensable. The latter enables the image data acquired by means of CT or MRT angiography to detect and evaluate the respective movement sequences in real time.

It is proposed in the three publications 03/043 516 A2, 04/051 572 A2 and 05/104 951 A1 that two markings of the balloon catheter or catheters used be employed as registration markers of the object of interest (vessel implant, e.g. stent). Balloon catheters have a radio-opaque and MRT-active marking at both their proximal and also at their distal end (balloon marker $M_P$, $M_D$) which thus delimit the balloon catheter axially. If the respective markers are registered in consecutive images, the objects of interest of these images can also be registered, i.e. moved, turned of stretched (scaled) so that these come lie on top of each other as closely as possible and can finally be averaged.

The averaging obliterates the background and in particular greatly reduces the noise, so that the object increases in contrast. However this process requires the basic assumption that the actual object of interest (the stent) moves exactly and is linearly scaled like the respective imaging of the balloon marker. This is in fact the case if a rigid connection between the stent and the balloon is assumed, but this does not represent the general case. In general the balloon does not remain in the inflated state after the placement of the stent, since this would result in a blocking of the blood flow or because of the contrast media filling would impede the visibility the stent meshes.

In actual fact there are frequently small relative movements of the stent in relation to the balloon markers. With longer stents in particular the result can be a partial separation of the balloon from the stent on one side caused by the process of deflating the balloon. Often the relative movement then represents a movement of the marker or markers in the radial direction relative to the stent. As already mentioned, movements in the order of magnitude of the stent mesh diameter (appr. 0.01 mm) are sufficient to make an image of the stent unusable or to prevent it.

SUMMARY OF THE INVENTION

The object of the present invention is thus to provide a method which improves the presentation of vessel implants.

This object is achieved in accordance with the invention by the features of the independent claim. The dependent claims develop the central ideas of the invention in an especially advantageous manner.

Inventively a method is thus claimed for high-resolution presentation of device implants in angiographic recordings, which features the following steps:
S1: Recording at least two images of an object-catheter combination, including catheter markers, with a medical imaging method
S2: Detection of an ROI created in the form of a surface between the balloon markers which completely contain the object to be registered for each image recorded
S3: Coarse registration of the ROI images by registration of the respective pairs of balloon markers of all recorded images
S4: Fine registration of the ROI image content/of the ROI image by registration of the ROI content.
S5: Arithmetic averaging across the fine-registered images Advantageously the catheter represents a balloon catheter which can be expanded with air or (contrast media-enriched) liquid.

The object advantageously represents a vessel implant in the form of a braided stent.

Also advantageously the surface lying between the catheter markers represents a rectangle.

The coarse registration is undertaken inventively by movement and/or turning and/or scaling of the marker connecting lines.

The fine registration is inventively based on one of the following measurement methods: Correlation-based measurement, sum of the absolute difference values, sum of the difference squares, variance of the difference, leading-sign-change based measuring, coincident bit counting, difference-histogram-based measuring.

It is particularly advantageous in the sense of an especially effective coarse and fine registration for the imaging to be ECG-triggered.

Furthermore a device is claimed which is suitable for executing a method according to the above-mentioned claims.

Likewise a computer software product is further claimed which implements a method in accordance with the above mentioned claims, when it is running on a computing device connected to a magnetic resonance tomography device, an x-ray image device or a projection radiography device.

BRIEF DESCRIPTION OF THE DRAWINGS

Further advantages, features and characteristics of the present invention are explained in greater detail below on the basis of exemplary embodiments which refer to the accompanying drawings.

DETAILED DESCRIPTION OF THE INVENTION

Figure 1:
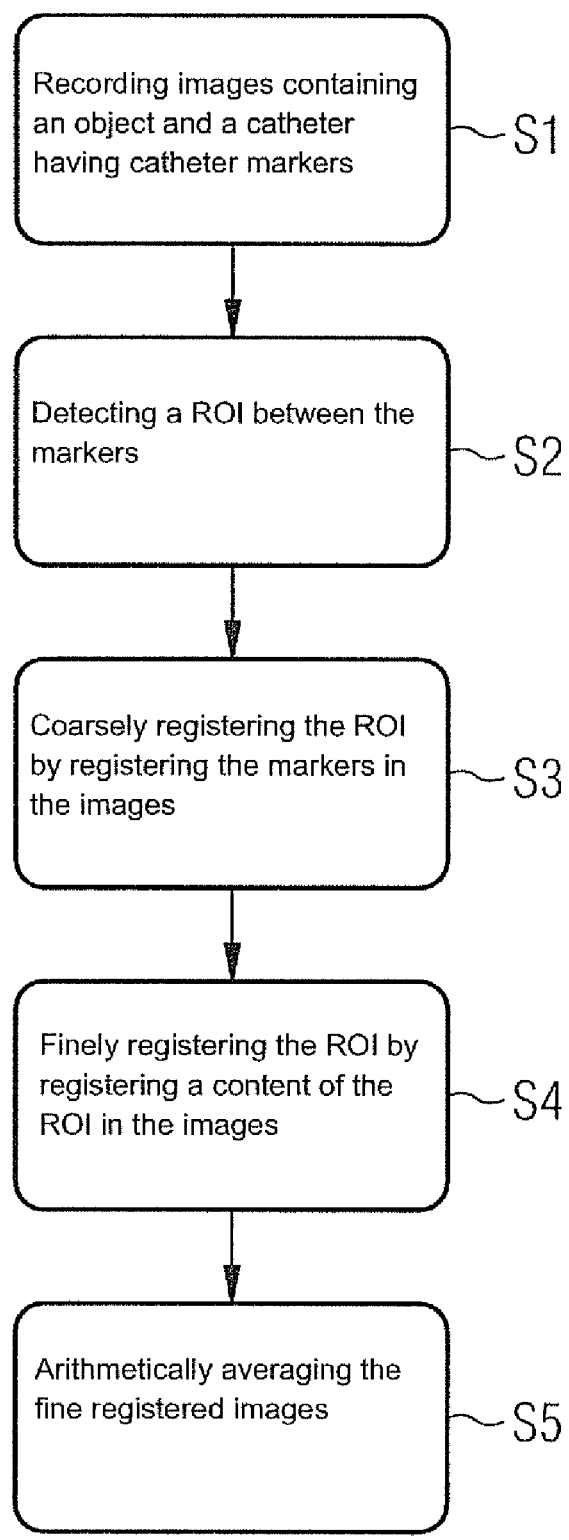
FIG. 1 shows a flowchart of the method in accordance with the invention.

FIG. 1 shows a flowchart of the inventive method. The object of the inventive method is to undertake a type of fine registration at the actual object of interest of a series of images and to use the (balloon) marker registration only as a type of coarse pre-registration. The complete registration process therefore breaks down into a number of steps:

In a first step S1 the series of images is first recorded. This is done with any given medical Imaging modality which is suitable for creating informative images of the object of interest (e.g. stent 18) with the balloon markers A,B. The imaging modality 11 might for example be projection radiography, CT, MRT, US etc.

In a second step S2 an ROI (Region Of interest) is created in each image of the series of images and this is region is created (e.g. manually) in the form of a rectangle lying between the markers A, B of the balloon which entirely surrounds or entirely contains the object to be registered.

It can now be that because of a movement of the patient (breath movement, heart movement, other movement) the object (e.g. stent 18) changes its position, size and location during the recording of the series of images.

For this reason, in a further step S3 a coarse pre-registration of the ROI images is undertaken, in that the respective pairs of markers of all images (A,B),(A',B') (by movement, turning, scaling) are registered and all ROIs come to coincide more or less well with each other.

The precise registration—a fine registration by obtaining very exact coverage of the same area (congruence) of the object images—is implemented in the penultimate step S4 by the content of the ROI images being registered.

In order, as already mentioned, to obliterate the background in order to thus greatly reduce the noise and exclusively increase the contrast of the object, in a last step S5 an averaging of the fine-registered images is undertaken.

Both for coarse pre-registration in accordance with step S3 and also for averaging in accordance with step S5 in document WO 05/104 951 A1 proposals are made which correspond to the most recent prior art. Methods for fine registration are generally identified as non-marker-based registration methods and are for example to be found in "Erik H. W. Meijering, Wiro J. Niessen, Max A. Viergever: Retrospective Motion Correction in Digital Subtraction Angiography: A Review; IEEE Transactions on Medical Imaging, vol. 18, no. 1, January 1999, pp".

Possible methods of coarse pre-registration are specified in document 05/104 951 A1 already mentioned.

A direct fine registration alone—without the knowledge of the rough position and location of the object (stent 18) in the image—represents a less robust image processing method. As a rule a stent 18 which is only slightly visible cannot automatically, i.e. purely mathematically, be found in an image without initial measures having been taken beforehand.

The great advantage of the inventive method lies in the fact that the ROI (Region Of Interest) can be adapted in an optimum manner to the object to be registered. A better detection of the edges of the object to be registered enables the user to minimize the ROI surface needed for fine registration, so that this non-marker-based fine registration obtains more favorable general or initial conditions, since the relevant signal components (the surface of the object of interest) is increased on the total surface of the ROI.

It should be noted here that the method in accordance with the invention still requires the recording of a number of images or of a series of images. If the desired high-resolution registration does not succeed, the patient 1 (with radiological imaging methods) will still be subjected to a significant dose of radiation 13. Only a high success quota in the registration also justifies the application of a relatively high radiation dose 13.

The success quota can be significantly increased by ECG triggering 4. In this case the fact is exploited that the distortion of a vessel implant (of a stent 18) is dependent on the heart movement and thus on a corresponding continuously-measured ECG curve.

Figure 6:
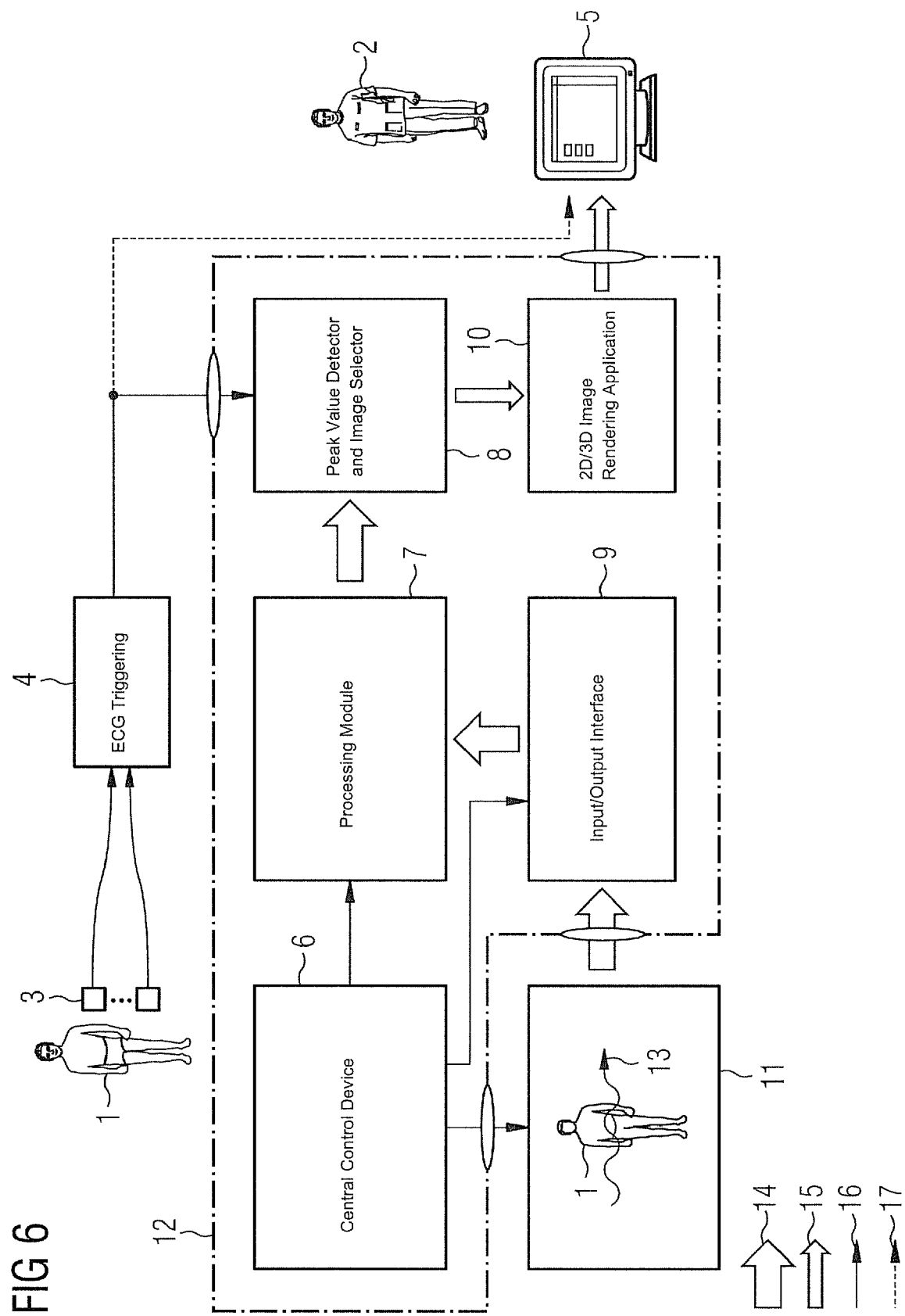
FIG. 6 shows a block diagram of a possible (ECG-triggered) system for executing the inventive method.

FIG. 6 shows a schematic block diagram of a possible ECG-triggered system (device) which is suitable for executing the inventive method with ECG triggering, i.e. which is capable of visualizing intravascularly-introduced vessel implants (stents 18) in high-resolution for specific heart phases. For this purpose a number of images in the form of an angiographic image series are recorded by a medical imaging modality 11 (CT, MRT, US, etc.) and fed to an image processing system BVS 12 via an input/output interface (I/O) 9. The image processing system BVS 12 comprises, in addition to a central control device ZSE 6, units such as a processing module VVM 7 with a digital filter for noise reduction, contrast enhancement and edge detection as well as a 2D/3D-image rendering application BRA 10 for reconstruction of an image of the vessel implants 18, with their visualization being implemented on a display screen AB 5. The central control device ZSE 6 controls the data exchange both with the imaging modality 11 and also with all further system components of the BVS 12. After the image data is received by the imaging modality 11 this is stored in an image data memory (not shown). A copy of this image data is fed via the input/output interface I/O 9 to the preprocessing module VVM 7.

In the case of an ECG-triggered acquisition of a series of images the ECG signal (in general a continuous voltage curve) is fed to a peak value detector and image selector SD/BS 8. This obtains from the voltage potentials reflecting the heart activity the heart phase information needed for undertaking the image selection. This heart phase information involves specific points in time (e.g. maximum values) of specific ECG triggers recurring in high-grade similar form. The SD/BS 8 only selects those angiograms which have been acquired at the same points in time of different heart cycles.

The stream of image data selected in this way produces a series of similar images which are then fed to the 2D/3D image rendering application BRA 10 which, within the framework of a coarse preregistration, registers the balloon marker pairs A,B, A',B' of all images of the series to each other.

After all pairs of points A, B, A', B' of successive, selected and overlaid angiograms have been aligned with each other in pairs, the objects likewise detected by the BRA 10 in the marked surfaces (as a rule the rectangles ROI, ROI' entirely containing the objects drawn manually, e.g. by means of the mouse by the user on the AB 5) undergo fine registration.

A subsequent arithmetical averaging across the gray values of these images leads to better image results compared to the individual images of the series. The reason for this lies in the fact that image details shown in the background are obliterated and high-frequency noise overlaid in the images is greatly reduced. This improves the contrast signal-to-noise ratio in the averaging image.

After completed fine registration and averaging the central control device ZSE 6 of the image processing system BVS 12 causes the stent implant 18 of which the image is to be recorded and the coronary tissue surrounding this image to be graphically visualized in two- and/or three-dimensional rendered form on the display screen AB 5 (optionally together with the recorded ECG curve).

The image numbers of the selected angiograms (which represent either the image series itself or a subset of the same) can—likewise be written at the instigation of the central control device ZSE 6—into a standardized data format (e.g. DICOM) via the input/output interface I/O 9 of the image processing system BVS 12 into a report file.

To summarize, the inventive method will be illustrated below with reference to FIGS. 2 to 5.

Figure 2:
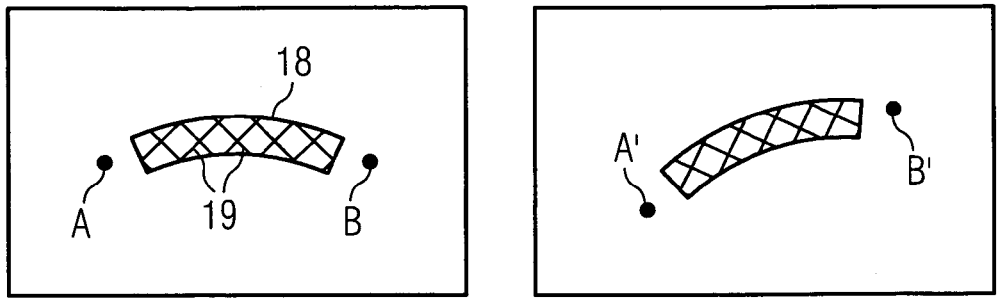
FIG. 2 shows two images of a series with a stent.

FIG. 2 is a greatly simplified diagram showing just two images (e.g. CT or MRT images) of a series of images, each with a filigree wire-mesh stent 18 (the meshing 19 is symbolized by crosses). The stent 18 is in both images slipped or pushed over a balloon catheter which is not shown itself for reasons of clarity.

Only the (balloon) markers A and B in the first image, or A' and B' in the second image arranged on both sides of the catheter are imaging (active) as a rule. Because of one or more overlaid anatomical movements (generally any movement of the patient, breathing, peristalsis, in most cases however heart movement) there is a more or less heavy deviation of the visible objects in both images in relation to each other, which is articulated in a distortion, movement and/or scaling.

Figure 3:
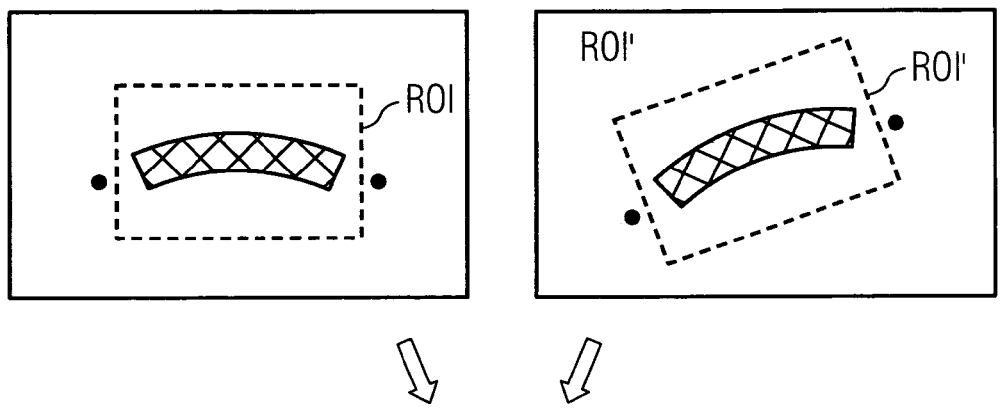
FIG. 3 shows the respective creation of an ROI (Region Of Interest)

Before however within the framework of the inventive method a (balloon) marker-based coarse pre-registration is undertaken, the stent in accordance with FIG. 3 is fully covered in both images by a rectangular surface (ROI, ROI'), lying between the markers, i.e. both stents 18 are entirely contained respectively in the respective rectangular region (ROI or ROI'). The ROI (the rectangle) can either be created manually (e.g. by means of a mouse on the screen by the user) or also automatically, by the height being estimated by the expected maximum deflection of the stent (e.g. 40% of the width; the width is given by the marker spacing). The coarse preregistration is undertaken by registering the pairs of markers (A, A') and (B, B') using the geometrical operations already mentioned above such that the pairs coincide exactly with each other after the end of the registration (FIG. 4).

Figure 4:
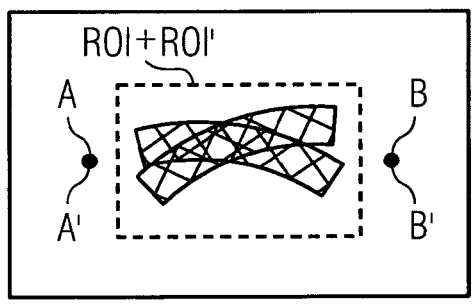
FIG. 4 shows the coarse registration based on the balloon markers.

For reasons of clarity the two object-containing rectangles (ROI, ROI') are also drawn in the case of FIG. 4 lying precisely one over the other. In the general case these, like the stents 18 themselves, are not identical, but—even if only slightly, but still enough to be taken into account—turned, scaled, moved etc. in relation to one another.

The rectangles—these can also be other areas or frames, e.g. ellipsoids or circles—i.e. the ROIs (here ROI, ROI') are however important, in order for fine registration to be able to exclusively be restricted solely to the objects to be registered, which are finally to be shown in high resolution.

Figure 5:
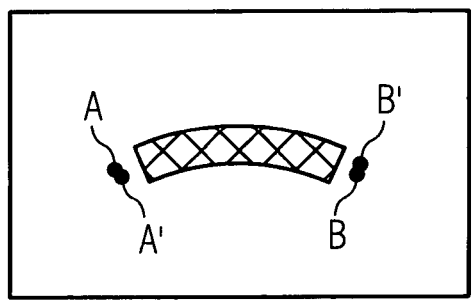
FIG. 5 shows the result of the registration after completion of the inventive method.

FIG. 5 finally shows the result of the inventive method based on a coarse-fine registration with subsequent averaging of the fine-registered images:

The stent meshes 19 (wire diameter appr. 1/10 mm) lie exactly over each other (which produces an extremely sharp image) but not the markers. The congruence of the markers after the coarse pre-registration (FIG. 4) would be destroyed or canceled again by the fine registration (FIG. 5).

The most important aspect of the inventive method is however that solely the actual object of interest (the stent 18 with its meshes 19) is shown sharply.

With a method according to the prior art (see the first three documents, the WO publications already cited) although the markers A, A' or. B,B' coincide precisely, the actual stent meshes 19 of interest do not, which would negate the object of the invention.

In summary, the steps of the inventive method are as follows:

S1 Recording of a (if necessary ECG-triggered) series of images which contain an object-balloon catheter combination, especially its respective balloon marker combination with a medical imaging method (CT, MRT, US, etc.)

S2 Detection of an ROI created in the form of a rectangle lying between the balloon markers, which entirely contains the object to be registered for each image of the series of images S3 Coarse preregistration of the ROI images by registering (movement, turning, scaling) the respective balloon marker pairs of all images S4 Fine registration of the ROI images by registering the rectangles or the ROI image content S5 Arithmetic averaging of the fine-registered images.

The invention claimed is:

1. A method for creating a high-resolution image of an object in an angiographic image of a patient, comprising:
   recording at least two images of the object and a catheter combination including catheter markers;
   detecting a region of interest in an area between the markers completely containing the object in the at least two images;
   marker-based coarsely registering the region of interest by registering the markers in the at least two images;
   non-marker-based finely registering the region of interest by registering a content of the region of interest in the at least two images after the marker-based coarse registration to increase a surface of the object on a total surface of the region of interest for generating a fine-registered image; and
   creating the high-resolution image of the object by arithmetically averaging across the fine-registered image,
   wherein the fine registration is undertaken by a method selected from the group consisting of: sum of difference squares, variance of difference, leading-sign-change based measuring, coincident bit counting, and difference-histogram-based measuring.

2. The method as claimed in claim 1, wherein the catheter is a balloon catheter.

3. The method as claimed in claim 1, wherein the area between the markers is a rectangle.

4. The method as claimed in claim 1, wherein the coarse registration is undertaken by moving, turning, or scaling connecting lines of the markers.

5. The method as claimed in claim 1, wherein the at least two images are ECG-triggered recorded.

6. The method as claimed in claim 1, wherein the at least two images are recorded by a magnetic resonance tomography device, an x-ray imaging device, or a projection radiography device.

7. The method as claimed in claim 1, wherein the object comprises a vessel implant of the patient.

8. The method as claimed in claim 7, wherein the vessel implant comprises a braided stent.

9. A device for creating a high-resolution image of an object in an angiographic image of a patient, comprising:
   an image device that records at least two images of the object and a catheter combination including catheter markers; and
   a computing device connected to the image device that:
      detects a region of interest in an area between the markers completely containing the object in the at least two images;
      marker-based coarsely registers the region of interest by registering the markers in the at least two images;
      non-marker-based finely registers the region of interest by registering a content of the region of interest in the at least two images after the marker-based coarse registration to increase a surface of the object on a total surface of the region of interest for generating a fine-registered image; and
      creates the high-resolution image of the object by arithmetically averaging across the fine-registered image,
   wherein the fine registration is undertaken by a method selected from the group consisting of: sum of difference squares, variance of difference, leading-sign-change based measuring, coincident bit counting, and difference-histogram-based measuring.

* * * * *